United States Patent
Vanoppen et al.

(10) Patent No.: US 7,026,269 B2
(45) Date of Patent: Apr. 11, 2006

(54) METALLIC HYDROGENATION CATALYSTS, PRODUCTION AND USE THEREOF

(75) Inventors: Dominic Vanoppen, Schifferstadt (DE); Michael Veith, St. Ingbert (DE); Kroum Valtchev, Saarbruecken (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/312,873

(22) PCT Filed: Jul. 4, 2001

(86) PCT No.: PCT/EP01/07650

§ 371 (c)(1),
(2), (4) Date: Jan. 2, 2003

(87) PCT Pub. No.: WO02/02233

PCT Pub. Date: Jan. 10, 2002

(65) Prior Publication Data

US 2003/0144553 A1     Jul. 31, 2003

(30) Foreign Application Priority Data

Jul. 4, 2000 (DE) ................... 100 32 303

(51) Int. Cl.
*B01J 23/70* (2006.01)

(52) U.S. Cl. ............ 502/327; 502/331; 502/332; 502/335; 502/336

(58) Field of Classification Search ........ 502/337, 502/327, 331, 332, 335, 336
See application file for complete search history.

(56) References Cited

U.S. PATENT DOCUMENTS

| | | | |
|---|---|---|---|
| 3,663,635 A | 5/1972 | Lassau et al. ........ | 585/275 |
| 4,042,615 A * | 8/1977 | Vannice et al. ........ | 502/337 |
| 4,762,959 A | 8/1988 | Mauldin et al. ........ | 585/640 |

FOREIGN PATENT DOCUMENTS

| | | |
|---|---|---|
| BE | 0737 574 | 2/1970 |
| DD | 284 371 | 11/1990 |
| DE | 1944382 | 9/1969 |
| DE | 2205521 | 8/1972 |
| DE | 2327230 | 5/1973 |
| EP | 0 168 096 | 1/1986 |
| GB | 832 153 | 4/1960 |
| WO | 00 51727 | 9/2000 |

OTHER PUBLICATIONS

J. Hesse et al.: "Different susceptibilities of nanosized single-domain particles derived from magnetisation measurements" Journal of Magnetism and Magnetic Materials, vol. 212, No. 1-2, pp. 153-167 Mar. 2000.

M. Veith et al.: "Molecular precursor approach to nano-scaled ceramics and metal/metal oxide composites" Nanostructured Materials, vol. 12, No. 1-4, pp. 191-194 1999.

Disseration of E.W. Fritscher Universitat des Saarlands, pp. 118-140 1997.

* cited by examiner

*Primary Examiner*—Stuart Hendrickson
(74) *Attorney, Agent, or Firm*—Oblon, Spivak, McClelland, Maier & Neustadt, P.C.

(57) ABSTRACT

The catalyst can be prepared by reduction of a precursor of a hydrogenation-active metal, which may be present on an oxidic support, by reaction with at least one compound of the formula (I)

$$H_nM(OR)_{3-n} \qquad (I)$$

where
M is Ga or Al,
R is $CR'_3$ or $SiR'_3$ where R' is $C_{1-20}$-alkyl, and
n is 1 or 2,
or dimers or oligomers thereof, wherein the crystallite size of the hydrogenation-active metal in the finished catalyst is from 5 to 30, preferably 5 to 15 nm.

9 Claims, No Drawings

METALLIC HYDROGENATION CATALYSTS, PRODUCTION AND USE THEREOF

The present invention relates to metallic hydrogenation catalysts which are particularly suitable for the hydrogenation of aromatic nitro compounds to give aromatic amines but can also be used for further reductive aminations, dehydrogenations or isomerizations.

Polyurethanes are frequently produced by reacting aromatic diisocyanates with diols. The aromatic diisocyanates can be prepared by nitration of appropriate aromatic compounds, subsequent hydrogenation of the nitro groups to amino groups and finally reaction of the amino groups with phosgene to form isocyanate groups. For example, toluene can be nitrated by reaction with nitric acid to form dinitrotoluene, after which the nitro groups are hydrogenated and converted into isocyanate groups. In the hydrogenation, the nitro groups should be hydrogenated in high yield and as selectively as possible without hydrogenation of the aromatic rings occurring.

Raney catalysts are frequently used as hydrogenation catalysts. The most readily available and therefore most widely used Raney catalyst is Raney nickel.

Raney nickel is obtained by alloying nickel with aluminum, silicon, magnesium or tin and, after mechanical comminution, decomposing the alloy by means of KOH. This leaches out the catalytically inactive metal and leaves a black metal sponge of the catalytically active nickel. However, the Raney nickel obtained in this way is pyrophoric owing to the large free surface area of the metal, so that it can only be handed under protective gas or in inert diluents. Raney nickel is frequently prepared freshly immediately before use, since a large loss in activity occurs during storage under inert diluents. A catalyst which has been deactivated by oxidation cannot be regenerated.

Attempts have also been made to obtain active catalysts from appropriate metal salts or metal complexes by activation with or canoaluminum compounds, cf., for example, BE-A-0 737 574. For example, a nickel complex is activated in the liquid phase using $AlH(Ot-Bu)_2$.

In place of Raney nickel, it is also possible to use supported nickel catalysts. These are generally prepared by impregnating the support with a nickel compound or coprecipitating the support and nickel compound. The catalyst obtained in this way has to be activated before use in order to convert the nickel oxide into metallic nickel. This forms a pyrophoric nickel having a high surface area, which has to be passivated and reactivated before use.

In DD-A-284 371, an attempt is made to circumvent disadvantages of the known nickel catalysts by oxidizing the surface of a coarse nickel catalyst in air and thus making it able to be handled in air. Before use in hydrogenation reactions, the catalyst is introduced into an inert liquid and milled to a fine powder. This operation once again has to be carried out under a hydrogen or inert gas atmosphere.

Nano Structured Materials, Vol. 12, 1999, pages 191 to 194, describes the preparation of ceramics and metal/metal oxide composites in nano-scale starting from molecular precursors.

$Ni/Al_2O_3$ is prepared by reducing NiO with $[H_2Al(O\text{-tert.-Bu})]_2$. The particle size of the nickel crystallites is 50 to 100 nm. By employing $[Ni\{Al(O\text{-}i\text{-}Pr)_4\}_2]$ and employing a CVD-process $Ni/Al_2O_3$ could be prepared in a nano scale. The nickel crystallites, however, show relatively large crystallite sizes in the range of from 50 to 100 nm.

The dissertation of E. W: Fritscher, Universität des Saarlandes, 1997, pages 118 to 140, relates to the same catalyst systems. The $Ni/Al_2O_3$ material is employed in the hydrogenation of styrene and maleic acid.

It is an object of the present invention to provide a hydrogenation catalyst, particularly for the hydrogenation of aromatic nitro compounds, which avoids the disadvantages of the known catalysts and, in particular, can be handled in air and be activated simply and has a high activity after activation. Activation should be possible at low temperatures.

We have found that this object is achieved by a catalyst which can be prepared by reduction of a solid precursor, e.g. an oxide and/or hydroxide, of a hydrogenation-active metal, which may be present on an oxidic support, by reaction with at least one compound of the formula (I)

$$H_nM(OR)_{3-n} \tag{I}$$

where
  M is Ga or Al,
  R is $CR'_3$ or $SiR'_3$ where R' is $C_{1-20}$-alkyl, and
  n is 1 or 2,
  or dimers or oligomers thereof, wherein the crystallite size of the hydrogenation-active metal in the finished catalyst is from 5 to 30 nm, preferably 5 to 15 nm. The hydrogenation-active metal can be selected from among all known hydrogenation-active metals. It is preferably selected from among metals of groups IA and VIIIA of the Periodic Table of the Elements and mixtures thereof. The hydrogenation-active metal is particularly preferably selected from among Fe, Co, Cu, Ni and Ru. In particular, it is Ni.

In the precursor, the metal can be present, for example, in the form of an oxide, hydroxide or a mixed oxide/hydroxide or else a carbonate or salt. Particular preference is given to NiO, especially having a crystallite size in the range of from 5 to 15 nm.

The metal oxide/hydroxide can be used without a support or in supported form. For example, it can be present on an oxidic support. Suitable oxidic supports are known. For example, the oxidic support can be selected from among $Al_2O_3$, $TiO_2$, $SiO_2$, $ZrO_2$ and mixtures thereof.

Further possible supports are metal sheets, gauzes, woven meshes, knitted meshes and monoliths made therefrom. The catalyst can be produced as a suitable supported structure which allows its use in hydrogenations in suspension, as a fixed bed, as powder (fluidized bed) or as coated supports.

Further suitable supports are zeolitic supports and monoliths made therefrom.

The object is furthermore achieved by a catalyst which can be prepared by reduction of a solid precursor of a hydrogenation-active metal present on an oxidic support, selected from $TiO_2$, $ZrO_2$ or mixtures thereof, by reaction with at least one compound of the general formula (I).

$$H_nM(OR)_{3-n} \tag{I}$$

where
  M is Ga or Al,
  R is $CR'_3$ or $SiR'_3$ where R' is $C_{1-20}$-alkyl, and
  n is 1 or 2, or dimers or oligomers thereof.

Preferably the crystallite size of the hydrogenation active metal in the final catalyst is 3 to 100 nm, preferably 3 to 30 nm, especially 5 to 15 nm.

In the compounds of the formula (I) or dimers or oligomers thereof, M is preferably Al. R is preferably $CR'_3$. R' is preferably $C_{1-12}$-alkyl, particularly preferably $C_{1-6}$-alkyl, in particular $C_{1-3}$-alkyl, for example methyl, ethyl, propyl or isopropyl. R' is especially methyl, so that R is tert-butyl. n is 1 or 2, preferably 2.

The compound of the formula (I) is preferably $H_2Al(OCR'_3)$ where R' is $C_{1-3}$-alkyl, especially methyl, or a dimer thereof. These compounds are known as alanes, in particular tert-butoxyalanes, and have been precisely characterized. Methods of preparing them are described, for example, in Z. anorg. allg. Chem. 1968, 358, 44 and Chem. Ber. 1996, 129, 381–384.

The dimers are cyclic compounds in which two Al atoms are bridged by O-tert-butyl radicals. According to the present invention, particular preference is given to using di(tert-butoxyaluminum dihydride) of this type.

The reduction, in particular of nickel oxide to nickel, is carried out by, in particular, reaction with di(tert-butoxyaluminum dihydride). The reaction can be carried out in suspension. However, the reaction is preferably carried out using the oxide and/or hydroxide of the hydrogenation-active metal, in particular nickel oxide, in the form of a solid and the compound of the formula (I) or the dimer or oligomer thereof, in particular di(tert-butoxyaluminum dihydride), in gaseous form. In the reaction, the supported or unsupported oxide/hydroxide of the hydrogenation-active metal is preferably agitated mechanically in order to achieve a uniform reduction.

The reduced catalyst contains a certain amount of Al from the reducing agent.

The gas-phase decomposition of di(tert-butoxyaluminum dihydride) over nickel oxide powder forms, for example, composites of the composition Ni/NiO/Al$_2$O$_3$/(Al) or Ni/Al$_2$O$_3$/(Al), depending on the reaction time. In this reaction, the nickel oxide is reduced by the hydride ligands. The aluminum oxide is formed in the pyrolysis of the precursor. In CVD processes using di(tert-butoxyaluminum dihydride) as precursor, Al/Al$_2$O$_3$ composite layers can be formed on a nickel substrate. Apart from a reduction of nickel oxide to metallic nickel, coating of the resultant nickel particles with the composite structure can also occur. However, the finished product generally contains significantly less aluminum than would be expected according to the stoichiometry. Small amounts of aluminum hydride or nickel hydride may also be present.

The amount of aluminum incorporated into the catalyst depends on any catalyst support used. The variation in the amount can be explained by the formation of relatively volatile aluminum-oxy-tert-butoxy compounds which are adsorbed to differing degrees on different supports.

As has been able to be shown by powder diffraction, nickel is present in the form of nanocrystalline phases. A possible aluminum oxide component is present in amorphous form. In the X-ray diffraction patterns, the reflections of metallic aluminum have a low intensity and are frequently difficult to discern above the background.

The Ni crystallite size can be controlled by means of the reaction temperature. The reaction is preferably carried out at from 20 to 600° C., particularly preferably from 200 to 500° C. At a reaction temperature of 400° C., for example, significantly smaller Ni crystallites are formed than at 500° C.

In the reaction, the compound of the formula (I) is preferably used in a molar ratio to oxide of the hydrogenation-active metal of from 0.1 to 10, particularly preferably from 0.3 to 3.

In the composite obtained after the reaction, crystallites of the hydrogenation-active metal are embedded and very finely dispersed in an AlO$_x$ matrix. The composites have properties which are similar to those of Raney nickel. However, unlike Raney nickel, they have the great practical advantage of being stable in air and nevertheless being able to be reactivated under very mild conditions (under reaction conditions). For the preparation of the catalysts further reference is made to the literature cited in the introduction.

For example, activation of passivated catalysts can be achieved at from 25 to 250° C., preferably from 25 to 120° C., and a hydrogen pressure in the range from 1 to 200 bar, preferably from 1 to 25 bar. In contrast, passivated Raney nickel catalyst cannot be reactivated. Likewise, an Ni/TiO$_2$ catalyst prepared by customary methods which has been passivated cannot be activated at 120° C.

Since activation of the catalysts of the present invention is possible under hydrogenation conditions, no separate activation step is necessary.

Since the catalysts of the present invention have activities similar to the activities of Raney nickel, they may be regarded as "dry" Raney catalysts which are stable under ambient conditions.

The present invention also provides a process for preparing the catalysts described, in which the process steps indicated are carried out.

In addition, the invention provides for the use of the catalyst described for the hydrogenation, dehydrogenation or isomerization of substituted or unsubstituted hydrocarbons. These can be aliphatic, aromatic or mixed aliphatic-aromatic hydrocarbons.

The catalyst of the present invention is preferably used for the hydrogenation of, for example, C—C double bonds, carboxyl groups, nitrites, imines, carboxylic acids and esters or aromatics. The invention also provides a process for preparing aromatic compounds containing amino groups by hydrogenation of corresponding aromatic compounds bearing nitro groups in the presence of a catalyst which is obtainable by reduction of a precursor of a hydrogenation active metal which may be present on an oxidic support, by reaction with at least one compound of the general formula (I).

$$H_nM(OR)_{3-n} \tag{I}$$

where

M is Ga or Al,

R is CR'$_3$ or SiR'$_3$ where R' is C$_{1-20}$-alkyl, and n is 1 or 2, or dimers or oligomers thereof.

Preferably the catalyst is composed as described above.

Examples of compounds which may be hydrogenated are dinitrotoluene, o-, p-nitrotoluene and nitrobenzene.

When the catalyst of the present invention has become exhausted in the reaction, it can be reactivated by known methods.

The invention is illustrated by the examples below.

EXAMPLE 1

Preparation of bis[(tert-butoxy)aluminum dihydride]

In a flask, 4.554 g (120 mmol) of LiAlH$_4$ are dissolved in 80 ml of diethyl ether. 5.334 g (40 mmol) of anhydrous aluminum trichloride are dissolved in 80 ml of diethyl ether in a second flask while cooling with liquid nitrogen, and this solution is then promptly added dropwise to the LiAlH$_4$ solution at room temperature. This results in precipitation of LiCl and the solution becomes turbid.

11.859 g (160 mmol) of tert-butanol are slowly added dropwise to the suspension formed above while cooling (0° C.), which results in vigorous evolution of hydrogen. The reaction solution is subsequently stirred at room temperature for another 2 hours. The LiCl formed is filtered off on a frit and the solvent is taken off under reduced pressure. The white residue is purified by sublimation at room temperature under reduced pressure (1 mbar) using a sublimation tube cooled by means of acetone/dry ice.

Yield: 15.2 g (93% of theory)

EXAMPLE 2

Preparation of the Catalyst

The preparation of the catalyst is carried out in a "hot wall" reactor. The powder to be coated is present in a glass tube which is connected at one end to the precursor reservoir and at the other end to a rotor unit. Rotation of the tube about its longitudinal axis achieves better mixing and uniform coating of the powder. The powder is heated by means of a tube furnace in which the reactor tube is located. To bring the precursor into the gas phase, vacuum is applied to the system. Owing to the ready volatility of the precursor, heating of the reservoir is not necessary. To achieve continuous mass transport, the CVD process is carried out under dynamic vacuum conditions. The volatile decomposition products are frozen out in a cold trap upstream of the vacuum pump.

Starting materials/conditions/result: 4.50 g of $NiO/TiO_2$ (Ni content: 30% by weight) 2.98 g of $[H_2AlOC_4H_9]$ Reaction at 400° C. Yield: 5.19 g of Ni/support Wet chemical elemental analysis: Ni: 31.77% by weight Al: 1.49% by weight The crystallite sizes of NiO and Ni determined by means of X-ray diffraction are shown for various catalysts in the table below.

TABLE 1

Volume average particle size, determined by the widths at half height of the reflections

| Starting powder $<D>_v^{NiO}/nm$ | Cat. sample/temperature/° C. $<D>_v^{NiO}/nm//<D>_v^{Ni}/nm$ |
|---|---|
| nano-NiO | Ni20Al/500° C. |
| 4.2 nm | ---//30 nm |
| nano-NiO | Ni30Al/450° C. |
| 4.2 nm | 4.0 nm//26 nm |
| polycrystalline NiO | Ni33Al/500° C. |
| >500 nm | 405 nm//20 nm |
| Starting powder $<D>_v^{NiO}/nm$ | Cat. sample/temperature/° C. $<D>_v^{NiO}/nm//<D>_v^{Ni}/nm$ |
| NiO on $TiO_2$ support | Ni38Al/500° C. |
| 10 nm | ---//20 nm |
| NiO on $TiO_2$ support | Ni43Al/400° C. |
| 10 nm | ---//12 nm |

The catalysts of the present invention are not pyrophoric and can be handled in air. Activation prior to the hydrogenation tests is not necessary.

EXAMPLE 3

Hydrogenation of Dinitrotoluene 220 ml of n-butanol and 0.8 g of the catalyst from Example 2 were placed in a 300 ml stirring autoclave. The catalyst was activated at 80° C. (or 120° C.) for six hours under 25 bar of hydrogen.

20 g of 2,4-dinitrotoluene were then introduced and hydrogenated at 80° C. under 25 bar of hydrogen. A pressure drop was observed as a result of the consumption of hydrogen, and further hydrogen was injected in each case. The activity of the catalyst was determined by means of the pressure to be reapplied per minute.

In the following table, the activity of catalysts according to the present invention is compared with the activity of known catalysts. In addition, catalysts activated after storage in air were examined. The results are summarized in Table 2 below.

TABLE 2

| Catalyst | Activity (bar/mm) |
|---|---|
| $Ni/TiO_2$, freshly reduced, exclusion of air (comparison) | 1.0 |
| $Ni/TiO_2$, passivated (comparison) | 0.0 |
| $Ni/TiO_2$, passivated, activated at 120° C. | 0.0 |
| $Ni/AlO_x/TiO_2$ (400° C.), 3 weeks in air | 0.17 |
| $Ni/AlO_x/TiO_2$ (400° C.), 3 weeks in air, activated at 80° C., 6 h | 1.0 |
| $Ni/Al/O_x/TiO_2$ (500° C.), 3 weeks in air | 0.22 |
| $Ni/AlO_x/TiO_2$ (500° C.), 3 weeks in air, activated at 80° C., 6 h | 0.44 |

The last four catalysts are catalysts according to the present invention. The temperature indicated in brackets refers to the reaction temperature in the preparation of the catalyst. The preparation of the catalysts was carried out as described in Example 2.

The results in table 2 show that the catalysts of the present invention can be activated readily even after prolonged storage in air.

We claim:

1. A process for preparing a catalyst by reduction of a metal compound, on an oxidic support, by reaction with at least one compound of the formula (I)

$$H_nM(OR)_{3-n} \qquad (I)$$

where
M is Ga or Al,
R is $CR'_3$ or $SiR'_3$ where R' is $C_{1-20}$-alkyl, and
n is 1 or 2,
or dimers or oligomers thereof.

2. A process as claimed in claim 1, wherein the reaction occurs with a molar ratio of metal source to compound (I) of from 0.1 to 10.

3. A process as claimed in claim 1, wherein the reaction occurs with a molar ratio of metal source to compound (I) of from 0.3 to 3.

4. A process as claimed in claim 1, wherein the reaction occurs at temperature of from 200 to 500° C.

5. A process as claimed in claim 1, wherein a metal of the metal compound is selected from the group consisting of Fe, Co, Cu, Ni, and Ru, and mixtures thereof.

6. A process as claimed in claim 1, wherein a metal of the metal compound is Ni.

7. A process for preparing a catalyst by reduction of a metal source by reaction with at least one gaseous compound of the formula (I)

$$H_nM(OR)_{3-n} \qquad (I)$$

where
M is Ga or Al,
R is $CR'_3$ or $SiR'_3$ where R' is $C_{1-20}$-alkyl, and
n is 1 or 2,
or dimers or oligomers thereof at a temperature in the range of from 200 to 500° C.

8. A process as claimed in claim 7, wherein a metal of the metal compound is selected from the group consisting of Fe, Co, Cu, Ni, Ru, and mixtures thereof.

9. A process as claimed in claim 7, wherein a metal of the metal compound is Ni.

* * * * *